United States Patent [19]
Galey et al.

[11] Patent Number: 5,834,518
[45] Date of Patent: Nov. 10, 1998

[54] USE OF N,N'-DIBENZYLETHYLENEDIAMINE-N,N'-DIACETIC ACID DERIVATIVES AS DEPIGMENTING AGENTS

[75] Inventors: Jean-Baptiste Galey, Aulnay-Sous-Bois; Laurent Marrot, Livry Gargan; Catherine Causse, Bourg La Reine, all of France

[73] Assignee: L'Oreal, Paris, France

[21] Appl. No.: 897,946

[22] Filed: Jul. 24, 1997

[30]     Foreign Application Priority Data

Jul. 26, 1996 [FR] France ................................ 96 09459

[51] Int. Cl.⁶ ........................ A01N 37/30; C07C 229/00
[52] U.S. Cl. ........................ 514/566; 562/442; 562/451
[58] Field of Search ................... 562/442, 451; 514/566

[56]             References Cited

FOREIGN PATENT DOCUMENTS

WO 94/11338   5/1994   WIPO .................. C07C 229/16

Primary Examiner—Paul J. Killos
Assistant Examiner—Brian J. Davis
Attorney, Agent, or Firm—Oblon, Spivak, McClelland, Maier & Neustadt, P.C.

[57]            ABSTRACT

Human skin is depigmented or bleached by applying thereto a compound of formula (1):

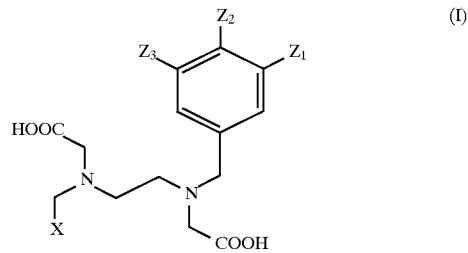

wherein X represents COOH or the ring:

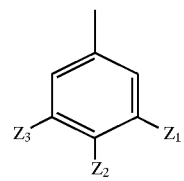

wherein $Z_1$, $Z_2$ and $Z_3$, independently of each other, are H, OR or R, R representing an optionally substituted saturated or unsaturated, linear or branched $C_1$–$C_8$-alkyl radical, or a salt, a metal complex or an ester of the compound.

4 Claims, No Drawings

USE OF N,N'-DIBENZYLETHYLENEDIAMINE-N,N'-DIACETIC ACID DERIVATIVES AS DEPIGMENTING AGENTS

BACKGROUND OF THE INVENTION

1. Field of the Invention

The present invention relate to the use of N,N'-dibenzylethylenediamine-N,N'-diacetic acid derivatives in a composition for topical application, as depigmenting and/or bleaching agents for human skin.

2. Description of the Background

The color of the skin depend on different factors and, in particular, the seasons of the year, race and sex, and it is mainly determined by the concentration of melanin produced by the melanocytes. In addition, at different periods in their lives, certain individuals develop dark and/or colored blemishes on the skin and more especially on the hands, making the skin non-uniform. These blemishes are also due to a large concentration of melanin in the keratinocytes at the skin surface.

For several years, attempts have been made to decrease and/or slow down the production of the melanin in order to depigment or bleach the skin, by acting on one or more of the points of the intracellular biochemical synthesis of melanin. In this regard, for many years, various molecules have been used and tested as depigmenting or bleaching agents.

The mechanism for the formation of skin pigmentation, that to say the formation of melanin, is particularly complex and schematically involves the following main steps: Tyrosine→Dopa→Dopaquinone→Dopachrome→Melanin Tyrosinase is the essential enzyme involved in this reaction sequence. It especially catalyses the reaction in which tyrosine is converted into dopa (dihydroxyphenylalanine) and the reaction in which dopa is converted into dopaquinone. Tyrosinase acts only when it is in the mature state, under the action of certain biological factors.

A substance is recognized as being depigmenting if it acts directly on the viability of the epidermal melanocytes in which melanogenesis takes place and/or if it interferes with one of the steps in the biosynthesis of melanin either by inhibiting one of the enzymes involved in melanogenesis or by becoming intercalated as a structural analogue of one of the chemical compounds in the melanin synthesis chain, whereby this chain may be blocked and ensure the depigmentation.

The substances most commonly used as depigmenting agents in compositions are, in particular, compounds such as vitamin C, vitamin C derivatives or vitamin E derivatives, arbutin, hydroquinone, kojic acid, placental derivatives and glutathione and its derivatives. These various compounds are known to act on the synthesis and/or activity of tyrosinase, the enzyme involved in the synthesis of melanin, or to reduce the amount of melanin formed or alternatively to stimulate the removal of melanin via the keratinocytes. Unfortunately, they are either toxic, as in the case of hydroquinone, or unstable in solution, as in the case of vitamin C and kojic acid, which complicates the manufacture of the composition somewhat, or else they may emit unpleasant odors and in particular sulfur odors in the case of glutathione, which consequently limits their use. Furthermore, these compounds are very limited in number.

Thus, there continues to be a need for a skin-bleaching agent which is as effective as the known agents, but which does not have their disadvantages, that is to say that it is stable in a composition, is non-toxic to the skin and has no unpleasant odor and especially insofar as this agent is applied to the skin.

In this regard copper-chelating agents have been used for a long time as depigmenting agents. Indeed, these chelating agents act on the copper ions present at the active site of tyrosinase, the key enzyme in melanogenesis. For example, it has been reported that L-mimosine, which is a natural hydroxypyridinone which forms very stable complexes with copper, is a good inhibitor of tyrosinase (Hider et al, Biochem. J. 1989, 257:289), as is kojic acid which also interacts strongly with copper. However, these chelating agents have the drawback of being toxic, especially L-mimosine, and of having side-effects associated with interference with the metabolism of certain metals.

On the other hand, much less work has been carried out with iron-chelating agents as depigmenting agents. Certain chelating agents are described as being capable of depigmenting mink skin (Blumenkrantz et al, Acta Agric. Scand. 1987, 37:375). However, the compounds described in this publication are toxic to a certain extent, which does not permit their topical use on human skin.

Moreover, lactoferrin hydrolysates have been patented as depigmenting agents (Morinaga, JP-A-04059714 and EP-A-438,750). However, the use of products of animal origin is to be avoided.

It is noted, however, that compounds, which are known as iron-chelating agents and which are commonly used in the cosmetic or dermatological field, have never been used to date to depigment or bleach the skin.

SUMMARY OF THE INVENTION

Accordingly, one object of the present invention is to provide a skin bleaching agent which effectively depigments the skin, but which is stable, is non-toxic to the skin and has no unpleasant odor.

Briefly, this object and other objects of the present invention as hereinafter will become more readily apparent can be attained in a method of depigmenting or bleaching human skin by treating the skin with a compound having formula (I):

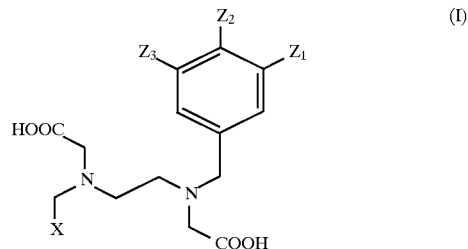

wherein X represents COOH or the ring:

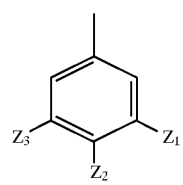

where $Z_1$, $Z_2$ and $Z_3$, independently of each other, are H, OR or R, R representing an optionally substituted saturated or unsaturated, linear or branched $C_1$–$C_8$ alkyl radical.

DETAILED DESCRIPTION OF THE PREFERRED EMBODIMENTS

It has now been found, unexpectedly, that certain iron-chelating agents have the property of inhibiting the synthesis of melanin and are thus able to act on skin pigmentation and blemishes without any risk of toxicity.

The $C_1$–$C_8$ alkyl radical is preferably a saturated $C_1$–$C_4$ radical such as methyl, ethyl, isopropyl or tert-butyl. Possible substituents for the alkyl groups include, for example, the hydroxyl group and the halogens.

The invention also includes the salts of these compounds, as well as their metal complexes and their acyl forms, for instance, esters such as the methyl ester or the ethyl ester.

Suitable salts include the addition salts with an inorganic or organic acid such as sulfuric acid, hydrochloric acid, nitric acid, phosphoric acid or acetic acid, and the addition salts with an inorganic or organic base such as sodium hydroxide, potassium hydroxide or triethanolamine.

Metal complexes which may be mentioned include the complexes formed by addition of $ZnCl_2$ or $CaCl_2$, for example.

The compounds of the invention may be prepared as described in WO 94/11338 filed in the name of the Applicants. In the application, the compounds of formula (I) are described as being useful for combating oxidative stress.

Compounds of formula (I) include, in particular, N,N'-di(3-hydroxy-benzyl)ethylenediamine-N.N'-diacetic acid and N,N'-di(3,4,5-trimethoxybenzyl)ethylenediamine-N,N'-diacetic acid.

It has now been discovered, surprisingly, that the compounds described herein have the advantage of possessing considerable depigmenting activity, while at the same time having none of the drawbacks of the compounds used previously.

The primary objective of the invention is, therefore, the use of at least one compound of formula (1), or a salt, a metal complex or an ester of such the compound, as a depigmenting and/or bleaching agent for human skin in a cosmetic composition.

An objective of the invention is also the use of at least one compound of formula (1), or a salt, a metal complex or an ester of such a compound, for the preparation of a dermatological composition intended for the depigmentation and/or bleaching of human skin.

Still another objective of the invention is a cosmetic and/or dermatological process for the depigmentation and/or bleaching of human skin, which consists in applying to colored and/or blemished skin at least one compound of formula (1), or a salt, a metal complex or an ester of such a compound in a cosmetically and/or dermatologically acceptable medium.

The effectiveness of the compound of formula (1) as a tyrosinase inhibitor is determined by evaluating its effect on the dopa-oxidase activity of human melanocyte tyrosinase. The compound tested is N,N'-di(3-hydroxybenzyl)ethylenediamine-N,N'-diacetic acid of formula (II):

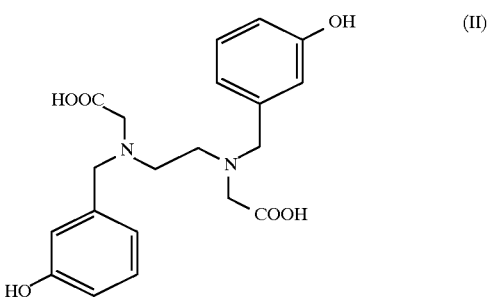

Human melanocytes are prepared and cultured and then introduced into media containing different, non-cytotoxic concentrations of the compound of formula (II) (0.1 mM, 0.25 mM, 0.5 mM and 0.75 mM). After three days, the melanocytes are "trypsinized" in a mixture of trypsin/0.05% EDTA/0.02% in a phosphate buffer (50 mM at pH 6.8), washed three times in the phosphate buffer containing 1% (w/v) Triton x-100 and subjected to ultrasound. After centrifugation, samples are taken and mixed with 5 mM L-dopa in phosphate buffer. The tyrosinase activity is evaluated by spectrophotometry by measuring the increase in the absorbance at 475 nm because of the formation of dopachrome from 5 mM dope. The absorbance is read on a microplate reader at 25° C. for 60 min.

The activity of the cellular tyrosinase is measured relative to a standard range prepared with commercial tyrosinase.

The results are as follows:

| Concentration of compound of formula (II) | 0 | 0.1 mM | 0.25 mM | 0.5 mM | 0.75 mM |
| --- | --- | --- | --- | --- | --- |
| Percentage of inhibition | 0 | 19% | 30% | 33% | 42% |

These results show that the compound of the invention exhibits good inhibition of tyrosinase and thus of melanin production.

The compound of formula (I) may be present in the composition of the invention in an amount ranging from 0.01 to 10%, preferably from 0.1 to 5% of the total weight of the composition.

The composition containing the compound of the invention contains a physiologically acceptable medium, that is to say, one which is compatible with the skin, the scalp and the hair, and more particularly constitutes a cosmetic and/or dermatological, in particular bleaching and/or depigmenting, composition for topical application.

The composition of the invention may be in any pharmaceutical form normally used for topical application, in particular in the form of an aqueous, aqueous-alcoholic or oily solution, an oil-in-water or water-in-oil or multiple emulsion, an aqueous or oily gel, a liquid, pasty or solid anhydrous product, a dispersion of oil in an aqueous phase with the aid of spherules, the spherules possibly being polymer nanoparticles such as nanospheres and nanocapsules or better still lipid vesicles of the ionic and/or nonionic type.

This composition may be relatively fluid and have the appearance of a white or colored cream, an ointment, a milk, a lotion, a serum, a paste or a foam. It may optionally be applied to the skin in aerosol form. It may also be in solid form and, for example, in the form of a stick. It may be used as a care product and/or as a make-up product for the skin.

The composition of the invention may comprise any excipients conventionally used in the cosmetic or dermatological field, in the usual concentrations. These excipients are chosen in particular from fatty substances, preserving agents, vitamins, gelling agents, fragrances, surfactants, water, antioxidants, fillers, hydrating agents, screening agents and mixtures thereof.

As fatty substances which may be used in the invention, mention may be made of mineral oils (liquid petrolatum), oils of plant origin (jojoba oil), oils of animal origin, synthetic oils (isopropyl palmitate), silicone oils (cyclopentadimethylsiloxane) and fluoro oils. Fatty alcohols (stearyl alcohol), fatty acids and waxes may also be used.

Suitable surfactants which may be used in the invention include, for example, fatty acid esters of polyethylene glycol such as polyethylene glycol stearate, and fatty acid esters such as sodium stearate.

Having generally described this invention, a further understanding can be obtained by reference to certain specific examples which are provided herein for purposes of illustration only and are not intended to be limiting unless otherwise specified.

The concentrations are given as percentages by weight.

Example 1: Bleaching Cream for the Face

| | |
|---|---|
| N,N'-di-(3-hydroxybenzyl)ethylenediamine N,N'-diacetic acid | 1% |
| sodium stearate | 3% |
| liquid petrolatum | 6% |
| preserving agent | 1% |
| cyclopentadimethylsiloxane | 2% |
| stearyl alcohol | 1% |
| fragrance | 1% |
| water | qs 100% |

When applied daily, the cream obtained enables the skin to be bleached.

Example 2: Bleaching Cream for the Hands

| | |
|---|---|
| N,N'-di(3-hydroxybenzyl)ethylenediamine N,N'-diacetic acid | 3% |
| jojoba oil | 13% |
| sipol wax | 6% |
| isopropyl palmitate | 2% |
| polyethylene glycol stearate | 3% |
| glycerol (hydrating agent) | 15% |
| preserving agent | 0.5% |
| fragrance | 1% |
| water | qs 100% |

The cream obtained may be used daily and is suitable for lightening blemishes on the hands, or even removing them altogether.

Obviously, numerous modifications and variations of the present invention are possible in light of the above teachings. It is, therefore, to be understood that within the scope of the appended claims, the invention may be practiced otherwise than as specifically described herein.

What is claimed as new and desired to be secured by Letters Patent of the United States is:

1. A method of bleaching, depigmenting or a combination thereof the human skin, comprising:

applying to the skin a compound of formula (I):

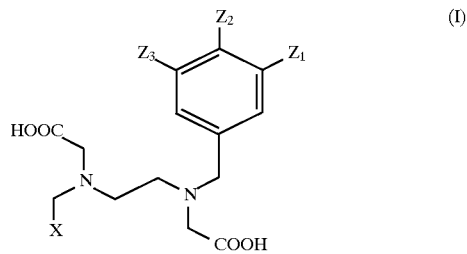

or a salt, an ester or a metal complex thereof, wherein x represents COOH or the ring:

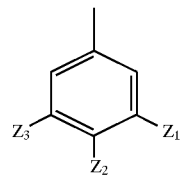

wherein $Z_1$, $Z_2$, and $Z_3$, independently of each other, are H or R, R representing a saturated or unsaturated, linear or branched $C_1$–$C_8$-alkyl radical or a substituted saturated or unsaturated, linear or branched $C_1$–$C_8$-alkyl radical.

2. A method of cosmetically or dermatologically treating the human skin, comprising:

applying to the skin a composition containing the compound of claim 1 thereby depigmenting or bleaching colored or blemished skin.

3. The method according to claim 2, wherein the amount of the active compound in said composition ranges from 0.01 to 10% of the total weight of the composition.

4. The method according to claim 3, wherein the compound of formula (I) is selected from the group consisting of N,N'-di(3-hydroxybenzyl)ethylenediamine-N,N'-diacetic acid and N,N'-di(3,4,5-trimethoxybenzyl)ethylenediamine-N,N'-diacetic acid.

* * * * *

UNITED STATES PATENT AND TRADEMARK OFFICE
CERTIFICATE OF CORRECTION

PATENT NO. : 5,834,518

DATED : November 10, 1998

INVENTOR(S): Jean-Baptiste GALEY, et al.

It is certified that an error appears in the above-identified patent and that said Letters Patent is hereby corrected as shown below:

Column 1, line 14, "depend" should read --depends--.

Signed and Sealed this

First Day of May, 2001

Attest:

NICHOLAS P. GODICI

Attesting Officer      Acting Director of the United States Patent and Trademark Office